United States Patent [19]

Portoghese et al.

[11] Patent Number: 5,578,725

[45] Date of Patent: Nov. 26, 1996

[54] DELTA OPIOID RECEPTOR ANTAGONISTS

[75] Inventors: Philip S. Portoghese, St. Paul, Minn.; Francine S. Farouz-Grant, San Francisco, Calif.

[73] Assignee: Regents of the University of Minnesota, Minneapolis, Minn.

[21] Appl. No.: 380,091

[22] Filed: Jan. 30, 1995

[51] Int. Cl.[6] .................................................. C07D 489/10
[52] U.S. Cl. .................................................................. 546/35
[58] Field of Search ............................. 514/279; 546/35, 546/37

[56] References Cited

U.S. PATENT DOCUMENTS

| | | | |
|---|---|---|---|
| 4,362,870 | 12/1982 | Portoghese | 542/403 |
| 4,401,672 | 8/1983 | Portoghese | 424/260 |
| 4,440,932 | 4/1984 | Kotick et al. | 546/44 |
| 4,649,200 | 3/1987 | Portoghese et al. | 546/26 |
| 4,806,556 | 2/1989 | Portoghese | 546/44 |
| 4,816,586 | 3/1989 | Portoghese | 544/340 |
| 5,223,507 | 6/1993 | Dappen | 514/279 |
| 5,225,417 | 7/1993 | Dappen | 514/279 |
| 5,244,904 | 9/1993 | Nagase et al. | 514/285 |
| 5,332,818 | 7/1994 | Nagase | 546/37 |
| 5,352,680 | 10/1994 | Portoghese et al. | 514/279 |
| 5,354,863 | 10/1994 | Dappen eta l. | 546/35 |
| 5,436,249 | 7/1995 | Dappen | 514/279 |
| 5,457,208 | 10/1995 | Portoghese et al. | 546/35 |
| 5,464,841 | 11/1995 | Portoghese | 546/37 |

FOREIGN PATENT DOCUMENTS

| | | | |
|---|---|---|---|
| 0456833A1 | 11/1990 | European Pat. Off. | |
| 94-07896 | 4/1994 | WIPO | 546/35 |

OTHER PUBLICATIONS

E. E. Abdelhamid et al., "Selective Blockage of Delta Opioid Receptors Prevents the Development of Morphine Tolerance and Dependence in Mice," *The Journal of Pharmacology and Experimental Therapeutics*, 258, 299–303 (1991).

K. Arakawa et al., "Immunosuppressive Effect of δ–Opioid Receptor Antagonist on Xenogenic Mixed Lymphocyte Reaction," *Transplantation Proceedings*, 24, 696–697 (Apr., 1992).

K. Arakawa et al., "The Immunosuppresive Effect of δ–Opioid Receptor Anagonist on Rat Renal Allograft Survival," *Transplant*, 53, 951–953 (1992).

K. Arakawa et al., "Delta Opioid Receptor Anatagonist for Immunosuppression After Rat Kidney Transplantation," *International Narcotics Research Conference*, p. 102, Abstract No. 018 (Jun. 24, 1992).

S. Botros et al., "Opioid Agonist and Antagonist Activities of Peripherally Selective Derivatives of Naltrexamine and Oxymorphamine," *J. Med. Chem.*, 32, 2068–2071 (1989).

D. R. Brown et al., "The Use of Quarternary Narcotic Antagonists in Opiate Research," *Neuropharmacology*, 24, 181–191 (1985).

E. J. Drower et al., "Selective Antagonism by Naltrindole of the Antinociceptive Effects of the Delta Opioid Agonist Cyclic [D–Penicillamine[2]–D–Penicillamine[5]] Enkephalin in the Rat," *The Journal of Pharmacology and Experimental Therapeutics*, 259, 725–731, (1991).

M. Erez et al., "Narcotic Antagonist Potency of Bivalent Ligands which Contain β–Naltrexamine. Evidence for Bridging Between Proximal Recognition Sites," *J. Med. Chem.* 25, 847–849 (1982).

J. H. Jaffe et al., "Opioid Analgestics and Antagonists," In:*The Pharmacological Basis of Therapeutics*, A. G. Gilman et al., (eds.) Peragamon Press, New York, Chapter 21, pp. 485–521 (1990).

H. Kataoka, "Novel Indolomorphinan Derivatives," Abstract No. 120798v, *Chemical Abstracts*, 73, 398 (1970).

W. R. Martin, "Pharmacology of Opioids," *Pharmacological Reviews*, 35, 283–323, (Dec. 1983).

S. L. Olmsted et al., "A Remarkable Change of Opioid Receptor Selectivity on the Attachment of a Peptidomimetnic κ Address Element to the δ Antagonist, Natrindole: 5'–[N[2] –Alkylamidino) methyl]naltrindole Derivatives as a Novel Class of κ Opioid Receptor Antagonists," *Journal of Medicinal Chemistry*, 36, 179–180 (1993).

P. S. Portoghese et al., "A Novel Opioid Receptor Site Directed Alkylating Agent with Irreversible Narcotic Antagonistic and Reversible Agonistic Activities," *J. Med. Chem.*, 23, 233–234 (1980).

(List continued on next page.)

*Primary Examiner*—Donald G. Daus
*Attorney, Agent, or Firm*—Schwegman, Lundberg, Woessner & Kluth, P.A.

[57] ABSTRACT

Compounds are provided of the formula:

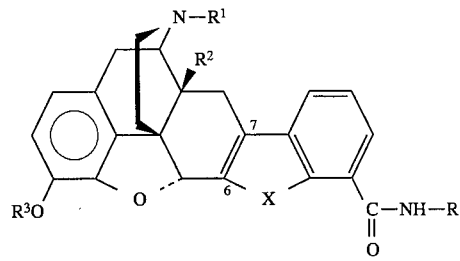

wherein
R[1] is ($C_1$–$C_5$)alkyl, $C_3$–$C_6$(cycloalkyl)alkyl, $C_5$–$C_7$(cycloalkenyl)alkyl, ($C_6$–$C_{12}$)aryl, ($C_6$–$C_{12}$)aralkyl, trans($C_4$–$C_5$)alkenyl, allyl or furan-2-ylalkyl, R[2] is H, OH or $O_2C$($C_1$–$C_5$)alkyl; R[3] is H, ($C_6$–$C_{10}$)aralkyl, ($C_1$–$C_5$)alky or ($C_1$–$C_5$)alkylCO; X is O, S or NY, wherein Y is H, benzyl or ($C_1$–$C_5$)alkyl; R is CH(Z)$CO_2$Y, wherein Z is H, $CH_2CO_2Y$ or $(CH_2)_nN(R^4)(R^5)$, wherein n is 1–5 and R[4] and R[5] are individually H, ($C_1$–$C_4$)alkyl, phenyl, (C=NH)$NH_2$, benzyloxycarbonyl or (C=NH$NO_2$); and the pharmaceutically acceptable salts thereof.

21 Claims, 1 Drawing Sheet

OTHER PUBLICATIONS

P. S. Portoghese et al., "Tena, A Selective Kappa Opioid Receptor Antagonist," *Life Sciences*, 36, 801–805 (1985).

P. S. Portoghese et al., "Application of the Message–Address Concept in the Design of Highly Potent and Selective Non-Peptide δ Opioid Receptor Antagonists," *J. Med. Chem.*, 31, 281–282 (Feb. 1988).

P. S. Portoghese et al., "Only One Pharmacophore is Required for the κ Opioid Antagonist Selectivity of Norbinaltorphimine," *J. Med. Chem.*, 31, 1344–1347 (1988).

P. S. Portoghese et al., "Naltrindole, a highly selective and potent non-peptide δ opioid receptor antagonist," *European J. of Pharma.*, 146, 185–186 (1988).

P. S. Portoghese, "Bivalent ligands and the message–address concept in the design of selective opioid receptor antagonists," *Trends Pharmacol. Sci.*, 10, 230–235 (Jun., 1989).

P. S. Portoghese et al., "Natrindole 5'-Isothiocyanate: A Nonequillibrium, Highly Selective δ Opioid Receptor Antagonist," *J. Med. Chem.*, 33, 1547–1548 (1990).

P. S. Portoghese et al., "Design of Peptidomimetic δ Opioid Receptor Antagonists Using the Message–Address Concept," *J. Med. Chem.*, 33, 1714–1720 (1990).

P. S. Portoghese et al., "Role of Spacer in Conferring κ Opioid Receptor Selectivity to Bivalent Ligands Related to Norbinaltorphimine," *J. of Med. Chem.*, 34, 1292–1296 (1991).

L. D. Reid et al., "Naltrindole, An Opioid Delta Receptor Antagonist, Blocks Cocaine–Induced Facilitation of Responding for Rewarding Brain Stimulation," *Life Sciences*, 52, PL67–71 (1993).

C. F. C. Smith, "16–Me Cyprenorphine (RX 8008M): A Potent Opioid Antagonist with some δ Selectivity," *Life Sciences*, 40, 267–274 (1987).

M. Sofuoglu et al., "Differential Antagonism of Delta Opioid Agonists by Naltrindole and its Benzofuran Analog (NTB) in Mice: Evidence for Delta Opioid Receptor Subtypes," *The J. of Pharma. and Experimental Thera.*, 257, 676–680 (1991).

A. E. Takemori et al., "The Irreverible Narcotic Antagonist and Reversible Agonistic Properties of the Fumaramate Methyl Ester Derivative of Naltrexone," *Eur. J. of Pharma.*, 70, 445–451 (1981).

A. E. Takemori et al., "Evidence for the Interaction of Morphine with Kappa and Delta Opioid Receptors to Induce Analgesia in β–Funaltrexamine–Treated Mice," *J. of Pharm. and Experimental Thera.*, 243, 91–94 (1987).

A. E. Takemori et al., "Nor–Binaltorphimine, A Highly Selective Kappa–Opioid Antagonist in Analgesic and Receptor Binding Assays," *J. of Pharma. and Exper. Thera.*, 246, 255–258 (1988).

S. J. Ward et al., "Improved Assays for the Assessment of κ– and δ–Properties of Opioid Ligands," *Eur. J. of Pharma.*, 85, 163–170 (1982).

M. S. Yamamura et al., "Characterization of [$^3$H]Naltrindole Binding to Delta Opioid Receptors in Rat Brain," *Life Sciences*, 50, PL 119–124 (1992).

DELTA OPIOID RECEPTOR ANTAGONISTS

BACKGROUND OF THE INVENTION

This invention was made with the assistance of the Government under a grant from the National Institutes of Health (Grant No. DA 01533-17). The U.S. Government has certain rights in the invention.

Endogenous opioid peptides are involved in the mediation or modulation of a variety of mammalian physiological processes, many of which are mimicked by opiates or other non-endogenous opioid ligands. Endogenous opioid peptides and opiates mediate their pharmacologic effects via interaction with opioid receptors both in the central nervous system (CNS) and peripheral nervous systems. See J. H. Jaffe et al., *Opioid Analgesics and Antagonists*, in *The Pharmacological Basis of Therapeutics*, A. G. Gilman et al., eds., Perganon Press, NY (1990) at pages 485–521. The principal target tissues in the central nervous system are the brain and the spinal cord. The major sites in the peripheral nervous system are the gastrointestinal tract, lymphocytes, and a variety of other tissues. The constipating action and inhibitory modulation of the immune response by morphine are examples.

D. R. Brown et al., *Neuropharmacol.*, 24, 181 (1986) employed quaternized opiates as pharmacologic tools in an attempt to isolate peripheral from central effects. However, these compounds exhibited considerably lower affinity for opioid receptors than their tertiary amine precursors. In an attempt to circumvent this problem, β-naltrexone and β-oxymorphamine incorporating hydrophilic groups attached to the C-6 position of the morphinan system were synthesized by S. Botros et al., *J. Med. Chem.*, 32, 2068 (1989). Botros et al. reported that such compounds, particularly opiates with zwitterionic moieties, exhibited substantially reduced access to the CNS without substantially decreasing receptor activity.

The fact that the effects of endogenous and exogenous opioids are mediated by at least three different types [mu (μ), delta (δ), kappa (κ)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types may be minimized or eliminated.

Some progress has been made in the development of highly selective opioid antagonists. For example, Portoghese et al. (U.S. Pat. No. 4,816,586) disclose certain opiate analogs which possess high selectivity and potency at delta receptors. Minimal involvement was observed at mu and kappa opioid receptors. One of the highly selective analogs disclosed in U.S. Pat. No. 4,816,586 has been named "naltrindole" or "NTI," and has the formula:

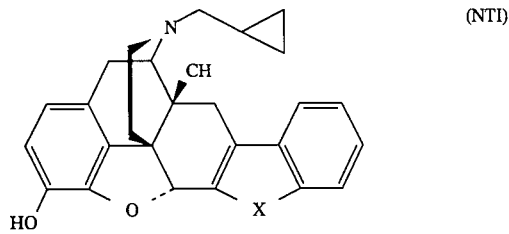

(NTI)

wherein

X is NH. See P. S. Portoghese et al., *J. Med.. Chem.*, 31, 281 (1988). Naltrindole has also recently been reported to have potent immunosuppressive activity. See, for example, K. Arakawa et al., *Transplantation*, 53, 951 (1992).

Therefore, a continuing need exists for compounds which are opioid receptor-selective, i.e., which can act as agonists or antagonists with specificity at the delta, mu or kappa opioid receptor, or at one of the subtypes of these receptors.

SUMMARY OF THE INVENTION

The present invention is directed to biologically active compounds of formula (I):

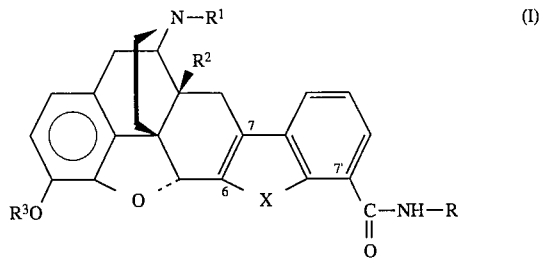

(I)

wherein $R^1$ is $(C_1–C_5)$alkyl, $C_3–C_6$(cycloalkyl)alkyl, $C_5–C_7$(cycloalkenyl)alkyl, $(C_6–C_{12})$aryl, $(C_6–C_{12})$aralkyl, trans$(C_4–C_5)$alkenyl, allyl or furan-2-ylalkyl; $R^2$ is H, OH or $O_2C(C_1–C_5)$alkyl; $R^3$ is H, $(C_6–C_{10})$aralkyl, $(C_1–C_5)$alkyl or $(C_1–C_5)$alkylCO; X is O, S or NY, wherein Y is H, benzyl or $(C_1–C_5)$alkyl; R is $CH(Z)CO_2Y$ wherein Z is H, $CH_2CO_2Y$, or $(CH_2)_nN(R^4)(R^5)$ wherein n is 1–5, preferably 3–4, and $R^4$ and $R^5$ are individually H, $(C_1–C_4)$alkyl, phenyl, (C=NH)$NH_2$, benzyloxycarbonyl or (C=NH)$NHNO_2$; preferably one or both of $R^4$ and $R^5$ are H; and the pharmaceutically acceptable salts thereof.

Using peptide antagonists of known binding selectivity as standards, it was found that the compounds of the invention are selective antagonists at delta opioid receptors, and that some are specific for the $δ_1$ or $δ_2$ subset of delta opioid receptors. All of the compounds preferably exhibit little or no binding at delta or mu receptors. Furthermore, compounds of the formula I were found to exhibit poor penetration into the central nervous system in in vivo animal models, while maintaining substantial peripheral effects. Thus, the present invention also provides a method for blocking delta opioid receptors in mammalian tissue or cells comprising said receptors, by contacting and complexing said receptors in vivo or in vitro with an effective amount of a compound of formula I, preferably in combination with a pharmaceutically acceptable vehicle. Thus, the compounds of formula I can be used as pharmacological and biochemical probes of opiate receptor structure and function, e.g., to measure the selectivity of other known or suspected opioid receptor antagonists or agonists at delta receptors. Procedures for such selectivity evaluations are disclosed hereinbelow, and in U.S. Pat. No. 4,816,586. Such tissue preferably includes tissue of the gut, the cardiovascular system, the lung, the kidney, reproductive tract tissue and the like. Circulating cells comprising delta opioid receptors include lymphocytes, and delta receptor agonists and antagonists, have also been implicated in immunoregulatory responses related to T cell function, such as immunosuppression.

Therefore, the compounds of formula I which exhibit delta receptor antagonist activity may also be therapeutically useful in conditions where selective blockage of delta receptors of non-CNS tissue or cells, is desired. Such conditions can include aspects of immunoregulation associated with pathological stimulation of the immune system, as in autoimmune disorders, and in immunosuppression associated with certain viral infections, or as induced during organ transplantation, as well as a variety of other physiological activities that may be mediated through delta receptors. See, for example, Portoghese et al. U.S. Pat. No. 08/149,039 filed Nov. 8, 1993, now U.S. Pat. No. 5,464,841, and references cited therein. Also, certain of the compounds of formula I are useful as intermediates for the formation of other bioactive compounds within the scope of formula I. These include benzyl esters of carboxylic acids and nitrated or benzyloxycarbonyl-protected amines that are a part of R.

The alkyl moiety present in the $R^1$ group which links the cycloalkyl, cycloalkenyl, aryl, or furan-2-yl moiety to the basic nitrogen atom in the compounds of formula I is a lower(alkyl) group, preferably —$(CH_2)_n$—, wherein n is about 1–5, most preferably n is 1, e.g., $R^1$ is $C_3$–$C_6$(cycloalkyl)methyl, $C_5$–$C_7$(cycloalkenyl)methyl, arylmethyl or furan-2-yl-methyl. Preferred aryl moieties include ($C_6$–$C_{10}$)aryl, i.e., phenyl, tolyl, napthyl, anisyl and the like.

In structure I, a bond designated by a wedged or darkened line indicates one extending above the plane of the $R^3O$- substituted phenyl ring. A bond designated by a broken line indicates one extending below the plane of the phenyl ring.

Preferred compounds of the formula I are those wherein $R^1$ is ($C_1$–$C_5$)alkyl, $C_3$–$C_6$(cycloalkyl)alkyl or $C_5$–$C_7$(cycloalkyl)methyl, and most preferably wherein $R^1$ is cyclopropylmethyl. $R^2$ is preferably OH or OAc ($O_2CCH_3$), and $R^3$ preferably is H. Preferably, X is NH, NHBz or $NCH_3$, most preferably NH. Preferably, R is CH(Z)$CO_2$H and Z is H, $(CH_2)_{3-4}NHR^4$ wherein $R^4$ is H or (C=NH)$NH_2$.

The ability of morphinan derivatives to cross the "blood-brain barrier" and to affect the central nervous system (CNS) is often far superior to that of peptide opioid antagonists. For example, as disclosed in U.S. patent application Ser. No. 07/750,109, filed Aug. 26, 1991, both NTI and its benzofuran analog, NTB were found to produce unexpectedly prolonged suppression of ethanol drinking in rats that were selectively bred for high voluntary ethanol drinking, as compared to peptidyl delta-opioid receptor antagonists. However, while the present compounds are also morphinan derivatives, the R group would be expected to be highly ionized, (in the ionic or zwitterionic form) at physiological pHs encountered in the mammalian gut. Thus, as discussed below, the access of these compounds to delta receptors in the CNS is restricted over previously known morphinans, including other NTI derivatives.

Processes of preparing the compounds of formula I are also aspects of the invention, as described hereinbelow, as are the novel intermediates employed in the syntheses, including compound 7, and its salts and esters.

DETAILED DESCRIPTION OF THE INVENTION

Figure 1:
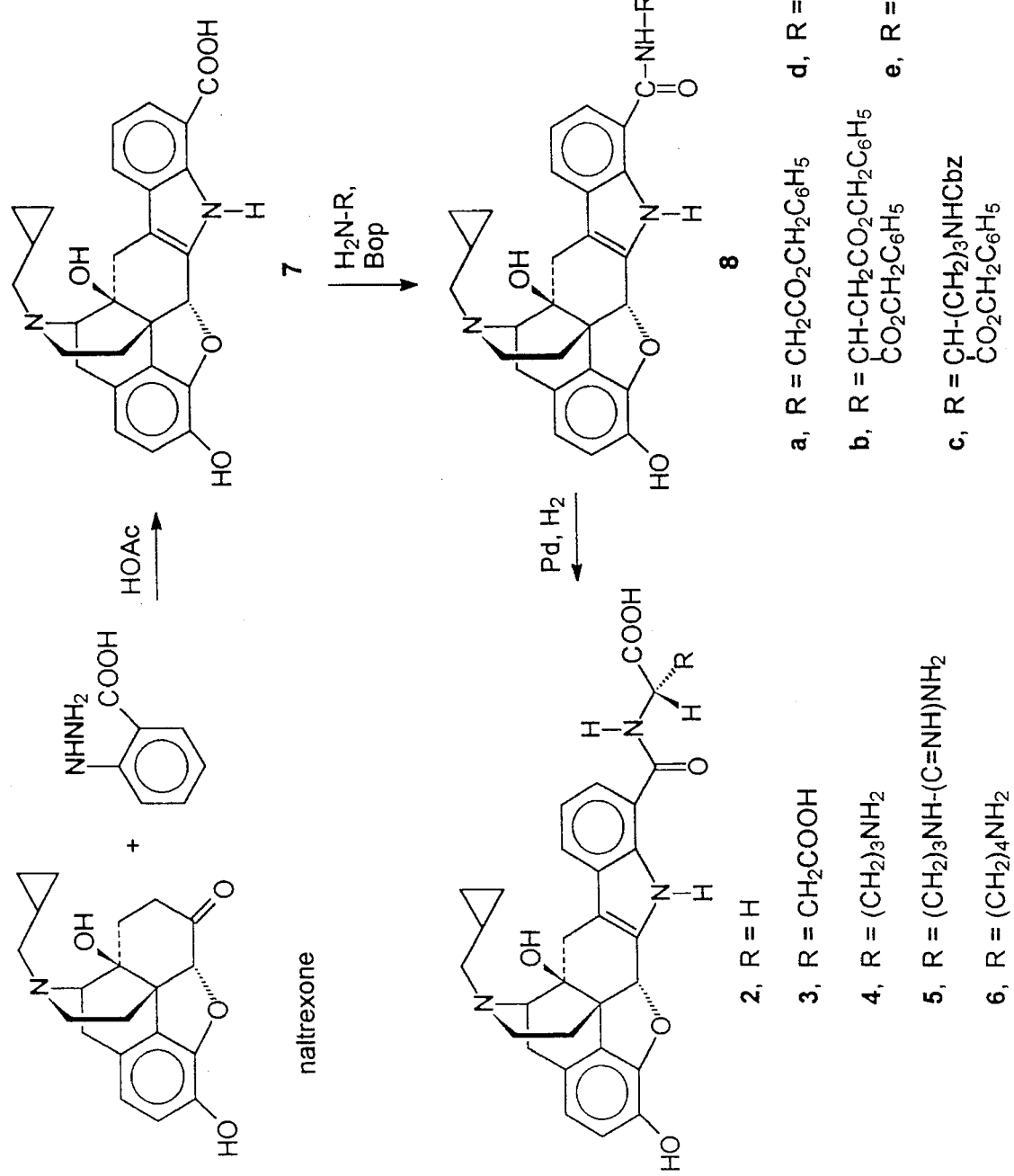
FIG. 1 is a schematic depiction of the synthesis of certain compounds of formula I.

Preparation of the compounds of formula I, which are formally N-substituted 7'-aminocarbonyl derivatives of NTI and its analogs, can be accomplished through amidation of a 7'-carboxyl group. Thus, as shown in FIG. 1, the key intermediate employed in the synthesis of target compounds 2–6 was 7'-carboxynaltrindole (7). Compound 7 was obtained via the Fischer indole synthesis which involved refluxing equivalent amounts of naltrexone and 2-hydrazinobenzoic acid in glacial acetic acid. See, B. Robinson, *The Fischer Indole Synthesis*, Wiley-Interscience, NY (1982). The nmr spectrum of 7 possessed the characteristic downfield absorption of H-5 due to deshielding by the indole moiety. The coupling of 7 with suitably protected amino acids using the Bop reagent, afforded the corresponding intermediates 8a–e. Catalytic hydrogenation of these intermediates gave target compounds 2–6.

Compounds of formula I wherein X is O, S or NY can be prepared from intermediates analogous to 7 or 8 wherein NH has been replaced by O, S or NY. These intermediates can be prepared as generally disclosed in U.S. Pat. No. 4,816,586, which is incorporated by the reference herein, which also discloses methods suitable for the preparation of salts of compounds of formula I.

The structures, common names and Merck Index reference numbers of representative 4,5-epoxy-6-ketomorphinan starting materials III, which can be used in place of naltrexone in the reaction scheme of FIG. 1, are summarized in Table I, below.

TABLE I

| $R^1$ | $R^2$ | $R^3$ | Common Name | Merck No.[2] |
|---|---|---|---|---|
| $CH_2CH(CH_2)_2$ | OH | H | naltrexone | 6209 |
| $CH_3$ | OH | H | oxymorphone | 6837 |
| $CH_3$ | H | H | hydromorphone | 4714 |
| $CH_3$ | H | $CH_3$ | hydrocodone | 4687 |
| $CH_2CH(CH_2)_2$ | H | H | — | —[1] |
| $CH_2CH=CH_2$ | OH | H | naloxone | 6208 |
| $CH_3$ | OH | $CH_3$ | oxycodone | 6827 |

[1]Preparation: M. Gates et al., J. Med. Chem., 7,127 (1964 ).
[2]The Merck Index, W. Windholz, ed., Merck & Co., Rahway, NJ (10th ed. 1983).

Other starting materials of the general formula III can be prepared by synthetic methods which are well known in the art of organic chemistry. For example, compounds wherein $R^1$ is H and $R^3$ is a suitable protecting group, and wherein the 6-keto group has also been protected, can be prepared from the compounds of formula III. These intermediates can be N-alkylated and deprotected to yield compounds of formula I wherein $R^1$ is $C_2$–$C_5$(alkyl), $C_4$–$C_6$(cycloalkyl)alkyl, $C_5$–$C_7$(cycloalkenyl)alkyl, aryl, aralkyl, trans-$C_4$–$C_5$alkenyl or furan-2-ylalkyl, by the application of well-known reactions.

For example, the free hydroxyl groups of the compounds of formula III, e.g., $R^2$=OH and/or $R^3$=H, can be protected by acid-labile groups such as tetrahydropyranlyl, trimethylsilyl, 1-methoxy-isopropyl and the like as disclosed in *Compendium of Organic Synthetic Methods*, I. T. Harrison et al., eds., Wiley-Interscience, New York, N.Y. (1971) at pages 124–131, (hereinafter "Compendium"). The protection of the 6-keto group of compounds or a thioketal group is disclosed in *Compendium*, at pages 449–453. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955).

Procedures for the alkylation of secondary amines with alkyl or aryl halides under basic or neutral conditions are well known. For example, see *Compendium* at pages 242–245; *Org. Synth.*, 43, 45 (1963); *J. Org. Chem.*, 27, 3639 (1962) and *J. Amer. Chem. Soc.*, 82, 6163 (1960).

Compounds of formula III wherein $R^2$ is acyloxy and/or $R^3$ is acyl can be prepared by using the corresponding starting materials on Table I. For example, naltrexone can be diacylated by reacting it with the appropriate $(C_1-C_5)$alkyl anhydride for 10–18 hrs at 18°–25° C. The resultant 3,14-diacylated compound can be converted to the 14-acylated compound by limited hydrolysis. The 3-acylated starting materials can be prepared by the short-term reaction of the compounds of Table I with the anhydride, e.g., for about 2–4 hours. The 3-acylated product can be separated from the 3,14-diacylated product by chromatography.

The acid salts of compounds of formula I wherein $R^3$=H, can be converted into the corresponding $(C_1-C_5)$alkoxy derivatives [$R^3$=$(C_1-C_5)$alkyl] by dissolving the starting material in DMF and adding an excess of the appropriate $(C_1-C_5)$alkyl iodide and an amine such as diisopropylethylamine. The reaction can be conducted at an elevated temperature for about 4–10 hours. The final product can be purified by column chromatography.

The invention also comprises the pharmaceutically acceptable salts of the biologically active compounds of formula I together with a pharmaceutically acceptable carrier for administration in effective, non-toxic dose form. Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. Physiologically acceptable carboxylic acid salts include alkali metal carboxylates and quaternatery ammonium salts. These physiologically acceptable salts are prepared by methods known in the art, e.g., by dissolving the free amine bases with an excess of the acid in aqueous alcohol, or neutralizing a free carboxylic acid with an alkali metal base such as a hydroxide; or with an amine.

In the clinical practice of the present method, the compounds of the present invention will normally be administered orally or parenterally, as by injection or infusion, in the form of a pharmaceutical unit dosage form comprising the active ingredient in combination with a pharmaceutically acceptable carrier, which may be solid, semi-solid or liquid diluent or an ingestible capsule or tablet. The compound or its salt may also be used without carrier material. As examples of pharmaceutical carriers may be mentioned tablets, intravenous solutions, suspensions, controlled-release devices such as patches or implants, microcapsules, liposomes and the like. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

The invention will be further described by reference to the following detailed examples, wherein melting points were taken using a Thomas-Hoover Melting Point apparatus in open capillary tubes, and are uncorrected. Elemental analyses were performed by M-H-W Laboratories, Phoenix, Ariz., and are within ±0.4% of the theoretical values. IR spectra were obtained on a Perkin-Elmer 281 infrared spectrometer and peak positions are expressed in $cm^{-1}$. NMR spectra were recorded at ambient temperature on GE-300 MHz and Bruker AC-200 MHz, and chemical shifts are reported as δ values (ppm) relative to TMS. Mass spectra were obtained on a VG 7070E-HF instrument. All TLC data were determined with E. Merck Art, 5554 DC-Alufolien Kieselgel 60 $F_{254}$. Column chromatography was carried out on E. Merck silica gel 60 (230–400) mesh). The eluents used during column chromatography and reverse phase preparative HPLC, $CHCl_3$-MeOH-$NH_4OH$ and MeOH-$H_2O$-$CH_3CN$, are denoted by CMA and MWA respectively. Dimethylformamide was distilled over calcium hydride. All other solvents and reagents were used without any further purifications unless specified. Naltrexone hydrochloride was supplied by Mallinckrodt.

EXAMPLE 1

7'-Carboxy-17-(cyclopropylmethyl)-6,7-dehydro-3,14-dihydroxy-4,5α-epoxy-6,7,2',3'-indolomorphinan hydrochloride (7)

Naltrexone hydrochloride (2.0 g, 5.3 mmol) and 2-hydrazinobenzoic acid (1.2 eq, 1.1 g) were dissolved in glacial acetic acid (75 mL). The reaction was refluxed for 6 hrs. The solvent was evaporated under reduced pressure and the residue dissolved in a minimum amount of MeOH. The crude product was purified on column chromatography (silica gel) with CMA 95:5:0.5. Upon evaporation of solvents under reduced pressure, the product was isolated as a solid which was recrystallized from methanol/ether, to afford 1.2 g of 7 (56%): mp>230° C.; $^1$H NMR (300 MHz, DMSO-$d_6$), δ 10.95 (d, 1H, COOH), 9.03 (s, 1H, PhOH), 7.75 (d, 1H, J=7.50 Hz, Ph), 7.61 (d, 1H, J=7.50 Hz, Ph), 7.04 (t, 1H, J=7.20 Hz, Ph), 6.45 (m, 2H, Ph), 5.63 (s, 1H, $H_5$), 3.15 (m, 3H, $H_9$, $H_{10}$), 2.90–2.60 (m, 8H, $H_8$ $H_{18}$ $H_{16}$ $H_{15}$), 1.62 (m, 1H, $H_{15}$), 0.58 (m, 1H, $H_{19}$), 0.51 (m, 2H, $H_{20}$, $H_{21}$), 0.42 (m, 2H, $H_{20}$, $H_{21}$); $^{13}$NMR (50 MHz, DMSO-$d^6$) δ 168.35, 143.11, 140.12, 131.04, 130.23, 127.70, 124.70, 123.53, 123.14, 118.57, 118.22, 117.28, 109.80, 83.39, 72.23, 61.40, 57.92, 46.78, 44.30, 29.97, 28.74, 23.10, 7.82, 4.41, 3.12; IR (KBr pellet) 3200, 1677 $cm^{-1}$; HRMS (FAB) 459 (M+H$^+$), calcd. 459.1919, obsvd 459.1911; Anal. ($C_{27}H_{26}O_5N_2 \cdot H_2O \cdot HCl$) C, H, N.

EXAMPLE 2

7'-Carboxamidoglycine-17-(cycloptopylmethyl)-6,7-dehydro-3,14-dihydroxy-4,5α-epoxy-6,7,2',3'-indolomorphinan benzyl ester (8a)

Carboxylic acid 7 (365 mg, 0.7 mmol) was dissolved in a mixture of DMF/$CH_2Cl_2$ (40 mL) (1:1), in the presence of $Et_3N$ (5.0 eq, 483 μL), benzotriazol-1-yloxytris(dimethylamino) phosphonium hexafluorophosphate (Bop reagent, Aldrich) (1.5 eq, 460 mg), and benzyl glycinate p-toluenesulfonate salt, (1.0 eq, 257 nag). The reaction mixture was extracted with ethyl acetate and the organic layer was washed with saturated $NaHCO_3$, 10% citric acid, and brine. The organic layer was dried over $MgSO_4$ and the solvent removed in vacuo. The crude product was eluted on a silica gel column with CMA (98:2:0.5) and purified further on preparative TLC (silica gel, 1 mm) with CMA (98:2:0.5). The desired product was isolated as an oil (150 mg, 36%)

which was crystallized from chloroform/hexanes: mp: 118°–121° C.; $^1$H NMR (300 MHz, CDCl$_3$) δ 10.16 (s, 1H, PhOH), 7.52 (d, 1H, J=7.50 Hz, Ph), 7.37 (m, 4H, Ph), 6.94 (d, 1H, H=7.20 Hz, Ph), 6.89 (m, 1H), 6.64 (d, 1H, J=8.40 Hz, H$_2$), 6.55 (d, 1H, J=8.50 Hz, H$_1$), 5.64 (s, 1H, H$_5$), 5.24 (s, 2H, COOBn), 4.29 (d, 2H, J=4.80 Hz, CH$_2$NH), 3.37 (d, 1H, J=6.00 Hz, H$_9$), 3.10 (d, 1H, J=18.30 Hz, H$_{10}$), 2.83–2.59 (m, 6H, H$_{16}$ H$_{18}$ H$_{10}$ NH), 2.45–2.29 (m, 3H, H$_{15}$ H$_8$), 1.80 (d, 1H, H=11.10 Hz, H$_{15}$), 0.87 (m, 1H, H$_{19}$), 0.55 (m, 2H, H$_{21}$, H$_{20}$), 0.16 (m, 2H, H$_{20}$, H$_{21}$); $^{13}$C NMR (75 MHz, CDCl$_3$) δ 171.43, 168.78, 163.45, 143.99, 140.22, 136.65, 135.89, 131.37, 130.92, 129.28, 129.25, 129.14, 129.11, 129.04, 128.57, 125.28, 123.65, 121.08, 119.48, 118.62, 118.12, 115.41, 111.35, 85.55, 73.49, 67.91, 62.89, 60.09, 48.66, 44.34, 42.18, 37.43, 37.19, 32.06, 29.32, 23.83, 10.09, 4.78, 4.42; HRMS (FAB) 606 (M+H$^+$), calcd 606.2604, obsvd 606.2625; Anal. (C$_{36}$H$_{35}$O$_6$N$_3$), C, N, N.

EXAMPLE 3

7'-Carboxamido-L-aspartate-17-(Cyclopropylmethyl)-6,7-dehydro-3,14-dihydroxy-4,5α-epoxy-6,7,2',3'-indolomorphinan dibenzylester (8b)

Carboxylic acid 7 (426 mg, 0.9 mmol) was dissolved in a mixture of DMF/CH$_2$CL$_2$ (40 mL) (1:1), in the presence of Et$_3$N (6.0 eq, 720 μL), Bop reagent (1.5 eq, 571 mg), and dibenzyl aspartate p-toluenesulfonate salt. The workup and purification were carried out as described for compound 8a. The desired product was isolated in 30% yield (187 mg, 0.2 mmol) and crystallized from chloroform/hexanes: mp: 115°–118° C.; $^1$H NMR (300 MHz, CDCl$_3$) δ 10.06 (s, 1H, OH), 7.59 (d, 1H, J=7.50 Hz, Ph), 7.32 (m, 7H, Ph), 7.13 (d, 11H, J=7.50 Hz, Ph), 6.85 (d, 1H, J=7.20 Hz, Ph), 6.76 (d, 1H, J=8.40 Hz, H$_2$), 6.65 (d, 1H, J=8.50 Hz, H$_1$), 6.13 (m, 1H, NH), 5.77 (s, 1H, H$_5$), 5.21 (m, 2H, CH$_2$Ph), 5.13 (m, 2H, CH$_2$Ph), 5.09 (m, 1H, CHN), 3.38 (d, 2H, J=4.80 Hz, CH$_2$COOBn), 3.26 (d, 1H, J=5.10 Hz, H$_9$), 3.21 (d, 1H, J=19.50 Hz, H$_{10}$), 2.89–2.71 (m, 3H), 2.57–2.33 (m, 5H), 1.84 (d, 1H, J=9.90 Hz, H$_{15}$), 0.87 (m, 1H, H$_{19}$), 0.55 (m, 2H, H$_{20}$, H$_{21}$), 0.17 (m, 2H, H$_2$O, H$_{21}$); $^{13}$C NMR (75 MHz, CDCl$_3$) δ 172.66, 172.26, 168.02, 143.81, 139.59, 136.34, 135.94, 135.58, 131.30, 129.30, 129.25, 129.11, 128.09, 128.02, 123.47, 121.48, 119.70, 118.09, 118.04, 117.85, 115.28, 115.25, 111.89, 86.31, 73.55, 68.61, 67.85, 62.84, 60.11, 49.83, 48.83, 44.37, 37.33, 32.44, 29.33, 23.83, 10.05, 4.78, 4.41; HRMS (FAB) M+H$^+$, calcd 754.3128, obsvd 754.3138.

EXAMPLE 4

7'-(Carboxamido-[N(δ)-carbobenzyloxy]-L-ornithinate)-17-(cyclopropylmethyl)-6,7-dehydro-3,14-dihydroxy-4,5α-epoxy-6,7,2',3'-indolomorphinan benzyl ester (8c)

Carboxylic acid 7 (426 mg, 0.8 mmol) was dissolved in a mixture of DMF/CH$_2$Cl$_2$ 1:1 (30 mL), at room temperature, in the presence of Bop reagent (1.5 eq, 536 mg), Et$_3$N (5.0 eq, 564 μL) and benzyl N(δ)-Cbz-L-ornithinate trifluoroacetate salt (380 mg, 0.8 mmol). The reaction mixture was stirred overnight. The workup and purification were carried out as described for compound 8a. The desired product was isolated as an oil 56% yield (362 mg): $^1$H NMR (300 MHz, CDCl$_3$) δ 10.09 (broad s, 1H, PhOH), 7.51 (d, 1H, J=8.70 Hz, Ph), 7.35 (m, 10H), 7.10 (d, 1H, J=8.30 Hz, Ph), 6.88 (m, 1H, Ph), 6.61 (d, 1H, H=8.40 Hz, H$_2$), 6.54 (d, 1H, J=8.40 Hz, H$_1$), 5.57 (s, 1H, H$_5$), 5.20 (m, 2H, COOBn), 5.06 (m, 2H, Cbz), 4.90 (m, 1H, CHCOOBn), 3.34 (d, 1H, J=6.30 Hz, H$_9$), 3.13 (m, 3H, H$_{10}$ —CH$_2$NHCbz), 2.81–2.57 (m, 3H, H$_{10}$, H$_{16}$), 2.45–2.32 (m, 4H, H$_8$, H$_{18}$), 1.76 (m, 6H, CH$_2$'s H$_{15}$), 0.90 (m, 1H, H$_{19}$), 0.57 (m, 2H, H$_{20}$, H$_{21}$), 0.17 (m, 2H, H$_{20}$, H$_{21}$); $^{13}$C NMR (75 MHz, CDCl$_3$) δ 172.56, 167.91, 156,87, 143.24, 139.55, 136.18, 139.55, 136.68, 136.18, 135.32, 130.67, 130.40, 128.64, 128.45, 128.30, 128.15, 127.98, 124.67, 123.29, 120.58, 118.84, 118.04, 117.50, 115.12, 110.99, 84.73, 72.81, 67.28, 66.60, 62.32, 59.47, 52.41, 48.06, 43.70, 40.48, 31.51, 29.52, 28.70, 26.21, 22.46, 9.47, 4.12, 3.81; NRMS (FAB) 797 (M+H$^+$), calcd 797.3550, obsvd 797.3547; IR (neat) 3300, 1719, 1703, 1613 cm$^{-1}$; Anal. (C$_{47}$H$_{48}$O$_8$N$_4$) C, H, N.

EXAMPLE 5

7'-(Carboxamido-N(ω,ω')nitro-L-argininate) 17-(cyclopropylmethyl)-6,7-dehydro-3,14-dihydroxy-4,5α-epoxy-6,7,2',3'-indolomorphinan benzyl ester hydrochloride (8d)

Carboxylic acid 7 (350 mg, 0.7 mmol) was dissolved in CH$_2$Cl$_2$/DMF (1:1) (50 mL), with Bop reagent (1.5 eq, 440 mg), Et$_3$N (5.0 eq, 463 mL), and benzyl N(α)-amino-N(ω, ω')-nitro-L-arginate trifluoroacetate salt (1.1 eq, 309 mg). The workup and purification steps were similar to those described for compound 8a. The desired product was isolated as a solid in 7% yield (33 mg); mp>240° C.; $^1$H NMR (300 MHz, CDCl$_3$) δ 10.01 (broad s, 1H, PhOH), 8.80 (broad s, 1H, OH), 7.63 (m, 1H, Ph), 7.47 (m, 6H, Ph), 7.05 (m, 1H, H$_5^1$), 6.68 (d, 1H, J=7.50 Hz, H$_2$), 6.55 (d, 1H, J=7.50 Hz, H$_1$), 5.67 (s, 1H, H$_5$), 5.18 (broad m, 2H, COOBn), 5.04 (m, 1H, CHCOOBn), 3.34 (d, 1H, J=6.30 Hz, H$_9$), 3.19 (m, 3H, H$_{10}$ —CH$_2$NH), 2.88–2.60 (m, 5H), 2.45–2.32 (m, 4H), 1.81 (m, 6H, CH$_2$'s H$_{15}$), 0.89 (m, 1H, H$_{19}$), 0.58 (m, 2H, H$_{21}$, H$_{20}$), 0.17 (m, 2H, H$_{20}$ H$_{21}$); $^{13}$C NMR (75 MHz, CDCl$_3$) δ 169.14, 167.04, 143.78, 140.22, 131.16, 129.07, 128.95, 128.80, 128.75, 125.10, 123.69, 121.59, 119.38, 118.83, 117.67, 111.05, 84.97, 73.58, 67.75, 62.71,125.39, 123.18, 121.87, 119.37, 118.96, 117.99, 117.91, 111.17, 84.78, 80.25, 73.32, 62.61, 59.69, 50.46, 48.35, 44.41, 42.36, 32.26, 29.74, 28.79, 23.71, 22.57, 10.32, 4.99, 4.52; HMRS (FAB) 573 (M+) cation, calcd 573.2713, obsvd 573.2711; Anal. (C$_{32}$H$_{37}$O$_6$N$_4$.HCl) C, H, H; Calcd H, 6.08. Found H, 6.59.

EXAMPLE 6

7'-(Carboxamido-[N(ε)-Carbobenzyloxy]-L-lysinate) 17-(cyclopropylmethyl)-6,7-dehydro-3,14-dihydroxy-4,5α-epoxy-6,7,2',3'-indolomorphinan benzyl ester (8e)

Carboxylic acid 7 (385 mg, 0.93 mmol) was dissolved in a mixture of DMF/CH$_2$Cl$_2$ (40 mL (1:1) (50 mL), in the presence of Et$_3$N (5.0 eq, 509 μL), Bop reagent (1.5 eq, 484 mg), and benzyl N(ε)-Cbz-L-lysinate trifluoroacetate salt (1.0 eq, 353 mg). The reaction was stirred overnight at room temperature. The workup and purification procedure was similar to that described for compound 8a. The desired product was isolated as an oil in 30% yield (170 mg); $^1$H NMR (300 MHz, CDCl$_3$) δ 10.12 (s, PhOH), 7.54 (d, 1H, J=8.70 Hz, Ph), 7.43 (d, 1H, J=7.20 Hz, Ph), 7.33 (m, 7H, Ph), 7.00 (m, 2H, Ph), 6.60 (d, 2H, J=8.00 Hz, H$_2$), 6.53 (d, 2H, J=8.00 Hz, H$_1$), 5.56 (s, 1H, H$_5$), 5.23 (m, 2H, COOBn), 5.04 (s, 2H, Cbz), 4.92 (m, 1H, CHCOOBn), 3.32 (d, 1H, J=6.20 Hz, H$_9$), 3.09 (m, 3H, H$_{10}$, CH$_2$NHCbz), 2.90–2.60 (bm, 3H, H$_{10}$, H$_{16}$), 2.50–2.30 (bm, 5H, H$_{16}$, H$_8$, H$_{10}$, H$_{18}$), 1.85 (bm, 3H, $H_8$ $CH_2$), 1.40 (bm, 6H, $H1_5$ $CH_2$'s), 0.90 (m, 1H, $H_{19}$), 0.58 (m, 2H, $H_{20}$ $H_{21}$), 0.17 (m, 2H, $H_{20}$ $H_{21}$); $^{13}C$ NMR (75 MHz, $CDCl_3$) δ 172.67, 167.83, 156.88, 143.24, 139.52, 136.62, 136.38, 135.57, 130.64, 130.54, 128.65, 128.45, 128.35, 127.99, 124.69, 123.32, 120.42, 118.80, 118.13, 117.40, 115.32, 110.95, 84.75, 72.75, 67.24, 66.62, 62.33, 59.48, 52.42, 43.71, 40.41, 31.89, 31.45, 29.25, 28.73, 23.14, 22.45, 9.46, 4.10, 3.81; HRMS (FAB) 811 (M+H$^+$), calcd 811.3706, obsvd 811.3716; IR (neat) 3200, 1743, 1721, 1637 cm$^{-1}$.

EXAMPLE 7

7'-(Carboxamidoglycine)-17-(cyclopropylmethyl)-6,7-dehydro-3,14-dihydroxy-4,5α-epoxy-6,7,2',3'-indolomorphinan hydrochloride (2)

Intermediate 8a (100 mg, 0.16 mmol) was dissolved in methanol (10 mL) in the presence of a catalytic amount (10%) of Pd-on-carbon and 2N HCl (1.5 eq, 12 μL). The hydrogenation reaction was run at atmospheric pressure for 1 hr. The mixture was filtered over celite and the celite washed several times with MeOH and the mixture was concentrated under reduced pressure. Slow addition of EtOAc concentrate led to the precipitation of a solid which was purified by HPLC using a $C_{18}$ reverse phase column (silica gel) with MWA 40:30:30 plus a few drops of $NH_4OH$ (Rt 50 mn). The crude product was purified by reverse phase HPLC (MWA 6:3:1), and the desired hydrochloride salt (Rt 11.87 mn) was isolated in 75% yield (68 mg): mp>240° C.; $Cl_2$/DMF (1:1) (50 mL), with Bop reagent (1.5 eq, 440 mg), $Et_3N$ (5.0 eq, 463 mL), and benzyl N(α)-amino-N(ω,ω')-nitro-L-arginate trifluoroacetate salt (1.1 eq, 309 mg). The workup and purification steps were similar to those described for compound 8a. The desired product was isolated as a solid in 7% yield (33 mg); mp>240° C.; $^1H$ NMR (300 MHz, methanol-$d_4$) δ 10.76 (bs, 1H), 7.61 (m, 2H, $H_6^1$, $H_4^1$), 7.06 (t, 1H, J=7.35 Hz, $H_5^1$), 6.64 (m, 2H, $H_1$ $H_2$), 5.75 (s, 1H, $H_5$), 4.15 (d, 2H, J=6.20 Hz, $CH_2N$), 3.47–3.27 (m, 2H, $H_9$ $H_{10}$), 3.18–2.86 (m, 4H, $H_{18}$, $H_{10}$, $H_8$), 2.77–2.67 (m, 2H, $H_8$, $H_{15}$), 1.94 (bd, 1H, J=13.50 Hz, $H_{15}$), 1.14 (m, 1H, $H_{19}$), 0.78 (m, 2H, $H_{20}$, $H_{21}$), 0.52 (m, 2H, $H_{20}$, $H_{21}$); $^{13}C$ NMR (75 MHz, methanol-$d_4$) δ 171.57, 169.58, 141.39, 130.79, 128.54, 123.23, 123.11, 123.00, 121.78, 121.75, 119.89, 118.89, 118.76, 109.01, 84.08, 72.80, 62.82, 58.01, 51.78, 41.32, 41.21, 29.43, 28.99, 24.22, 6.04, 5.44, 2.48; HRMS (FAB) 516 (M+H$^+$), calcd 516.2134, obsvd 516.2134; Anal. ($C_{29}H_{30}O_6N_3$·HCl) C, H, N.

EXAMPLE 8

7'-(Carboxamido-L-aspartate)-17-(cyclopropylmethyl)-6,7-dehydro-3,14-dihydroxy-4,5α-epoxy-6,7,2',3'-indolomorphinan hydrochloride (3)

Intermediate 8b (180 mg, 0.2 mmol) was dissolved in methanol (15 mL) in the presence of a catalytic amount (10%) of Pd-on-carbon and 6N HCl (2.0 eq, 0.5 μL). The hydrogenation and purification procedures are as described for compound 2. The crude product was purified by reverse phase HPLC (MWA 3:6:1), and the diacid (Rt 9.50 mn) was isolated in 90% yield (130 mg, 0.2 mmol): mp>210° C. (dec); $^1H$ NMR (300 MHz, DMSO-$d_6$) δ 11.04 (s, 1H, PhOH), 9.04 (broad s, 1H, OH), 8.38 (d, 1H, J=7.20 Hz, NH), 7.58 (d, 1H, J=7.50 Hz, Ph), 7.53 (d, 1H, J=7.50 Hz, Ph), 7.00 (t, 1H, J=7.50 Hz, Ph), 6.48 (s, 2H, $H_2$ $H_1$), 5.63 (s, 1H, $H_5$), 4.06 (m, 1H, CHCOOH), 3.45 (m, 1, $H_9$), 3.29 (d, 2H, J=3.60 Hz, $CH_2COOH$), 3.23–3.11 (m, 3H), 3.04–2.61 (m, 5H), 1.93 (d, 1H, J=11.10 Hz, $H_{15}$), 1.18 (m, 1H, $H_{19}$), 0.72 (m, 2H, $H_{20}$, $H_{21}$), 0.50 (m, 2H, $H_{20}$, $H_{21}$); $^{13}C$ NMR (75 MHz, DMSO-$d_6$) δ 174.63, 173.68, 167.07, 144.16, 141.09, 136.21, 132.16, 128.70, 123.19, 121.89, 119.62, 119.12, 118.30, 118.01, 110.03, 104.55, 104.13, 84.54, 73.28, 64.05, 62.47, 59.09, 50.01, 47.93, 45.50, 29.80, 24.02, 5.42, 4.23, 1.21; HRMS (FAB) 574 (M+H$^+$), calcd 574.2189, obsvd 574.2191; Anal. ($C_{31}H_{32}O_8N_3$·HCl) C, H, N.

EXAMPLE 9

7'-(Carboxamido L-ornithine)-17-(cyclopropylmethyl)-6,7-dehydro-3,14-dihydroxy-4,5α-epoxy-6,7,2',3'-indolomorphinan hydrochloride (4)

Intermediate 8c (233 mg, 0.3 mmol) was dissolved in MeOH (20 mL) with 1N HCl (3 drops, 1.0 eq) and a catalytic amount of 10% Pd-on-carbon. The hydrogenation and purification were similar to those described for 2. The product was isolated in 85% yield (155 mg): mp>240° C.; $^1H$ NMR (300 MHz, DMSO-$d_6$) δ 10.92 (s, PhOH), 8.70 (d, 1H, J=7.20 Hz, Ph), 7.67 (broad s, 1H, Ph), 7.61 (d, 1H,, J=7.20 Hz, Ph), 7.50 (d, 1H, J=7.50 Hz, Ph), 6.98 (t, 1H, J=7.50 Hz, Ph), 6.45 (s, 2H, NH), 5.60 (s, 1H, $H_5$), 4.36 (m, 1H, CHCOOH), 3.20–3.00 (m, 4H, $H_9$, $H_{10}$ $CH_2NH_2$), 2.90–2.40 (m, 8H, $H_8$, $H_{10}$, $H_{18}$, $H_{16}$, $H_{15}$), 1.90–1.70 (m, 5H, $H_{15}$ $CH_2$'s), 0.85 (m, 1H, $H_{19}$), 0.46 (m, 2H, $H_{20}$, H21), 0.12 (m, 2H, $H_{21}$, $H_{20}$); $^{13}C$ NMR (75 MHz, methanol-$d_4$) δ 171.16, 167.70, 144.13, 140.82, 136.30, 132.16, 132.05, 128.69, 6.70 (d, 1H, J=7.50 Hz, $H_2$), (d, 1H, J=7.50 Hz, $H_1$), 5.63 (s, 1H, $H_5$), 4.33 (m, 1H, CHCOOH), 3.35–3.12 (m, 4H, $H_9$ $H_{10}$ $CH_2NH$), 2.80–2.62 (m, 5H, $H_{10}$, $H_{18}$, $H_{16}$), 2.45–2.32 (m, 3H, $H_8$, $H_{15}$), 1.81–1.60 (m, 5H, $H_{15}$ $CH_2$'s), 0.85 (m, 1H, $H_{19}$), 0.46 (m, 2H, $H_{20}$, $H_{21}$), 0.12 (m, 2H, $H_{21}$, $H_{20}$); IR (KBr) 3200, 1735, 1644 cm$^{-1}$; HRMS (FAB) 617 (M+), calcd 617.3087, obsvd 617.3087; Anal. ($C_{33}H_{39}O_6N_6$·HCl) C, H, N.

EXAMPLE 10

7'-(Carboxamido-L-arginine)-17-(cyclopropylmethyl)-6,7-dehydro-3,14-dihydroxy-4,5α-epoxy-6,7,2',3'-indolomorphinan hydrochloride (5)

Intermediate 8d (33 mg, 0.04 mmol) was dissolved in MeOH (5 mL), with a catalytic amount (10%) of Pd on carbon, and HCl (3.0 eq, 100 μL). The hydrogenation and purification steps were as described for compound 2. The desired compound was isolated in 90% yield (20 mg); mp>250° C. (dec); $^1H$ NMR (300 MHz, DMSO-$d_6$) δ 10.05 (bs, 1H, PhOH), 7.38 (m, 3H, Ph), 59.88, 44.26, 41.08, 32.00, 29.09, 23.52, 9.74, 4.39, 3.89; IR (KBr) 3500, 1735, 1637 cm$^{-1}$; HRMS (FAB) 750 (M+H$^+$), calcd 750.3251, obsvd 750.3242.

EXAMPLE 11

7'-(N(α)-Carboxamido-L-lysine)-17-(cyclopropylmethyl)-6,7-dehydro-3,14dihydroxy-4,5α-epoxy-6,7,2',3'-indolomorphinan hydrochloride (6)

Intermediate 8e (170 mg, 0.2 mmol) was dissolved in MeOH (20 mL) in the presence of a catalytic amount (10%) of Pd-on-carbon and 1N HCl (3.0 eq, 600 mL). The hydrogenation and purification were as described for compound 2. The desired hydrochloride salt was isolated in 65% yield (82 mg); mp>270° C. (dec); $^1$H NMR (300 MHz, methanol-d$_4$) δ 7.64 (d, 1H, J=7.50 Hz, Ph), 7.57 (d, 1H, J=7.50 Hz, Ph), 7.05 (t, 1H, J=7.50 Hz, Ph), 6.61 (broad s, 2H, Ph), 5.73 (s, 1H, H$_5$), 4.16 (d, 1H, J=4.80 Hz, CHCOOH), 3.32–3.15 (m, 4H, H$_9$, H$_{10}$ CH$_2$), 3.04–2.97 (m, 3H, H$_{10}$ H$_{18}$ H$_{16}$), 2.87–2.67 (m, 4H, H$_{18}$ H$_{16}$ H$_8$), 1.96 (m, 4H, H$_{15}$ CH$_2$), 1.71 (m, 2H, CH$_2$), 1.51 (m, 2H, CH$_2$), 0.90 (m, 1H, H$_{19}$), 0.85 (m, 2H, H$_{21}$, H$_{20}$), 0.51 (m, 2H, H$_{20}$, H$_{21}$); $^{13}$C NMR (75 MHz, methanol-d$_4$) δ 174.95, 168.23, 144.20, 141.66, 136.41, 131.92, 130.29, 128.70, 123.45, 122.77, 122.55, 120.04, 119.09, 118.88, 117.39, 109.49, 84.03, 73.21, 62.08, 60.87, 57.85, 53.59, 47.07, 39.44, 31.01, 29.82, 29.33, 27.62, 24.70, 24.02, 6.86, 6.31, 3.65; HRMS (FAB) 587 (M+), calcd 587.2869, obsvd 587.2857; IR (KBr) 3300, 1728, 1637 cm$^{-1}$; Anal. (C$_{33}$H$_{39}$O$_6$N$_4$.HCl) C, H, N.

EXAMPLE 12

Pharmacological Results

A. Smooth Muscle Preparations

All target compounds were tested on the electrically stimulated guinea pig ileal longitudinal muscle (GPI) and mouse vas deferens (MVD) preparations as described previously by H. P. Rang, *J. Pharmacol. Chemother.*, 22, 356 (1965) and G. Henderson et al., *Brit J. Pharmacol.*, 46, 746 (1972), respectively, as reported in P. S. Portoghese et al., *Life Sci.*, 36, 801 (1986). Antagonists were incubated with the preparations for 15 min prior to testing. Morphine (M), ethylketazocine (EK), and [D-Ala$^2$,D-Leu$^5$]enkephalin$^{17}$ (DADLE) were employed as μ-, κ-, and δ-selective agonists, respectively. Morphine and EK were employed in the GPI, and DADLE was used in the MVD. The antagonist potencies mediated through δ opioid receptors were expressed as Ke values which were calculated from the equation, Ke= [antagonist]/(IC$_{50}$ ratio−1), where the IC$_{50}$ ratio represents the IC$_{50}$ of the agonist in the presence of the antagonist divided by the control IC$_{50}$ of the agonist in the same preparation.

As demonstrated by the data summarized on Table 2, compounds 2–6 were potent and selective δ opioid antagonists with Ke values ranging from 1–5 nM. None were more potent than NTI at δ receptors, but the δ-selectivities were equivalent to or higher than that of NTI. In contrast to the results reported by Dappen et al. in U.S. Pat. Nos. 5,354,863 and 5,225,417 for carboxy-substituted derivatives of NTI, the precursor 7 exhibited δ antagonist potency approaching that of NTI. Thus, compound 7 and the use of a compound of formula I wherein the NHR group is replaced by OH, to antagonize the activity of delta opioid receptor agonists are also within the scope of the invention.

TABLE 2

Antagonist Potencies of 7'-Substituted Amino Acid Conjugates of Naltrindole in the MVD and GPI Preparations

| Compd$^a$ | DADLE(δ)$^b$ | | M(μ)$^c$ | EK (κ)$^c$ | IC$_{50}$ Selectivity Ratio | |
|---|---|---|---|---|---|---|
| | IC$_{50}$ ratio | K$_e$ (nM)$^d$ | IC$_{50}$ ratio | IC$_{50}$ ratio | δ/μ | δ/κ |
| 1(NTI)$^e$ | 459 ± 104 | 0.2 | 11.2 ± 1.8 | 1.3 ± 0.2 | 41 | 353 |
| 2 | 32 ± 8 | 3.2 | 1.5 ± 0.1 | 1.1 ± 0.2 | 21 | 30 |
| 3 | 89 ± 20 | 1.1 | 1.3 ± 0.5 | 2.1 ± 0.6 | 67 | 43 |
| 4 | 58 ± 15 | 1.8 | 3.0 ± 1 | 0.9 ± 0.0 | 20 | 63 |
| 5 | 31 ± 5 | 3.3 | 1.3 ± 0.6 | 1.2 ± 0.5 | 24 | 27 |
| 6 | 20 ± 4 | 5.2 | 1.0 ± 0.4 | 1.1 ± 0.0 | 20 | 20 |
| 7 | 25 ± 7$^f$ | 0.4 | 2.0 ± 0.3 | 1.0 ± 0.2 | 122$^g$ | 231$^g$ |

$^a$The concentration of antagonist was 100 nM unless otherwise specified.
$^b$[D−Ala$^2$, D−Leu$^5$]enkephalin in the MVD preparation.
$^c$Morphine (M) or ethylketazocine (EK) in the GPI preparation.
$^d$Derived from the Schild relationship (Schild, H.O. Pharmacol. Rev., 9, 242 (1957)) and calculated from an average of at least three IC$_{50}$ ratio determinations by using K$_e$ = [antagonist]/(IC$_{50}$ ratio − 1).
$^e$Data from V.L. Korlipara et al., J. Med. Chem., 37, 1882 (1994).
$^f$The concentration of 7 in the MVD experiment was 10 nM.
$^g$A calculated IC$_{50}$ ratio (238) based on 100 nM of 7 was employed to calculate the selectivity ratio.

B. Receptor Affinity

The opioid receptor affinities of the target compounds were determined on guinea pig membranes employing a modification of the method of Werling et al., *J. Pharmacol. Exp. Ther.*, 233, 722 (1986). Binding to κ, μ, and putative "δ$_1$" and "δ$_2$" sites was evaluated by competition with [$^3$H]U69593, [$^3$H][D-Ala$^2$,MePhe$^4$,Gly-ol$^6$]enkephalin ([$^3$HDAMGO), [$^3$H][D-Pen$^2$-D-Pen$^5$]enkephalin ([$^3$H]DPDPE), and [$^3$H][D-Ser$^2$-Leu$^5$]enkephalin-Thr$^6$([$^3$H]DSLET), respectively. As shown by the data on Table 3, each of compounds 2–6 and the 7'-carboxy starting material 7 possessed high affinity for δ sites. The glycinate 2 nad precursor 7 possessed 2 and 6 times greater affinity for δ$_1$ sites than NTI, while other members (3–6) of the series had 5–10 fold less affinity than that of NTI.

All of the compounds were also highly selective, with Ki ratios substantially greater than that of NTI. It is noteworthy that the glycinate conjugate 2 possessed the highest selectivity ratios, with values of μ/δ$_1$ and κ/δ$_1$ in excess of 30,000. Interestingly, the glycine and ornithine conjugates (2 and 4) competed more effectively with [$^3$H]DSLET than with [$^3$H] DPDPE for δ sites by a factor of 8–10. The aspartate and lysine derivatives (3 and 6) exhibited a modest preference for [$^3$H]DPDPE sites. However, as discussed below, there is no clear correlation between binding and a specific pharmacologic antagonist potency in vitro or in vivo.

TABLE 3

Binding of 7'-NTI Derivatives to Guinea Pig Brain Membranes

| Compound | $K_i(nM)$[a] | | | | $K_i$ Selectivity Ratio | | |
|---|---|---|---|---|---|---|---|
| | μ | κ | $\delta_1$ | $\delta_2$ | $\mu/\delta_1$ | $\kappa/\delta_1$ | $\delta_1/\delta_2$ |
| 1 (NTI)[b] | 3.8 | 332 | 0.03 | | 127 | 11066 | |
| 2 | 206 | 162 | 0.005 | 0.00066 | 38166 | 30037 | 8.2 |
| 3 | 368 | 893 | 0.14 | 0.41 | 2574 | 6246 | 0.3 |
| 4 | 136 | 57 | 0.18 | 0.015 | 756 | 320 | 11.3 |
| 5 | 333 | 188 | 0.16 | 0.083 | 2096 | 1181 | 1.9 |
| 6 | 219 | 41 | 0.30 | 0.75 | 719 | 134 | 0.4 |
| 7 | 24 | 42 | 0.013 | 0.016 | 1846 | 3246 | 0.8 |

[a]The geometric mean of $K_i$ values from three replicate determinations for [³H]DAMGO, [³H]U69593, [³H]DPDPE, and [³H]DSLET, representing μ, κ, $\delta_1$ and $\delta_2$ sites, repectively.
[b]Data from P.S. Portoghese et al., J. Med. Chem., 33, 1714 (1990).

C. In Vivo Studies

Two of the more selective antagonist ligands (2, 3) and NTI (1) were evaluated in male Swiss-Webster mice using the tail-flick assay according to the methodology of F. C. Tulunay et al., J. Pharmacol. Exp. Ther., 190, 395 (1974). Mice were pretreated with the antagonist by the i.c.v. or i.v. route so that the peak antagonist activity coincided with the peak antinociceptive response of the selective agonists. The nonpeptide μ and κ agonists, morphine and trans-(±)-3,4-dichloro-N-methyl-N-[2-(1-pyrrolidinyl)cyclohexyl]benzeneacetamide (U50488), were administered s.c. (von Voigklander, J. Pharmacol. Exp. Ther., 224, 7 (1983)); the peptide agonists (DPDPE and DSLET) were injected i.c.v.

As shown by the data presented in Table 4, when administered either i.v. or i.c.v., the glycine conjugate 2 effectively antagonized the antinociceptive effect of the $\delta_1$ agonist, DPDPE. No significant antagonism of DSLET ($\delta_2$), morphine (μ), or U50488 (κ) was observed. Similarly, the aspartate conjugate 3 selectively antagonized DPDPE.

TABLE 5

Dose Required to Produce an Equivalent Antagonist of DPDPE-induced Antinociception[a]

| Compound | i.c.v. | i.v. | Ratio (i.v./i.c.v.) |
|---|---|---|---|
| 1 | 0.3 nmol/kg | 2.19 μmol/kg | 7,300 |
| 2 | 4.7 pmol/kg | 0.53 μmol/kg | 112,766 |
| 3 | 12.5 pmol/kg | 0.62 μmol/kg | 49,600 |

[a]Dose required to double the $ED_{50}$ of DPDPE (antagonist dose/$ED_{50}$ ratio − 1).

D. Discussion

The present invention provides polar δ-selective antagonists that are less accessible to the CNS after peripheral administration. Therefore, these compounds can provide useful tools to resolve the central from the peripheral effects mediated by δ opioid receptors.

The conjugates 2–6 and their precursor 7 were found to be potent δ opioid receptor antagonists in the mouse vas deferens preparation and they displayed little, if any, antagonism toward μ- and δ-selective agonists in the guinea pig ileum. In fact, the δ/μ and δ/κ $IC_{50}$ selectivity ratios of these ligands were equal to or greater than that of NTI.

Binding studies revealed that the Ki values of these antagonists were in the sub-nanomolar range for δ receptors. It is noteworthy that some of the conjugates (2, 4) appeared to have greater affinity for $\delta_2$ relative to $\delta_1$ putative binding sites, while others (3, 6) exhibited a modest preference for $\delta_1$ over $\delta_2$ sites. The fact that these binding selectivity ratios do not correlate with the in vivo $\delta_1/\delta_2$ selectivity ratios of 2 and 3, as discussed below, suggests that the binding data may be of limited value to predict pharmacologic potency of antagonists in these studies.

The glycinate 2 and aspartate 3 conjugates were evaluated for their effectiveness as antinociceptive agents in mice by peripheral (i.v.) and central (i.c.v.) routes of administration.

TABLE 4

Antagonist Profiles of Compounds 2 and 3 After Intracerebroventricular (i.c.v) and Intravenous (i.v.) Administration in Mice

| Agonist | Pretreatment[b] | | Control $ED_{50}$ (95% C.L.)[c] | $ED_{50}$ Ratio (95% C.L.)[d] |
|---|---|---|---|---|
| | Compound | Dose (Route of Injection) | | |
| Morphine (μ) | 2 | 20 pmol/kg (i.c.v.) | 9.7 (8.6–10.9) μmol/kg, s.c. | 0.9 (0.8–1.1) |
| | 3 | 20 pmol/kg (i.c.v.) | | 1.0 (0.7–1.5) |
| U50,488H (κ) | 2 | 20 pmol/kg (i.c.v.) | 27.3 (8.5–52.8) μmol/kg, s.c. | 0.8 (0.7–0.9) |
| | 3 | 20 pmol/kg (i.c.v.) | | 0.7 (0.4–1.2) |
| DSLET ($\delta_2$) | 2 | 20 pmol/kg (i.c.v.) | 0.7 (0.3–1.0) nmol, i.c.v. | 1.1 (0.8–1.6) |
| | 3 | 20 pmol/kg (i.c.v.) | | 0.5 (0.3–1.1) |
| DPDPE ($\delta_1$) | 2 | 20 pmol/kg (i.c.v.) | 8.6 (6.5–11.1) nmol. i.c.v. | 5.3 (3.6–7.7)* |
| | 3 | 20 omol/kg (i.c.v.) | | 2.6 (2.0–3.6)* |
| | 2 | 0.9 μmol/kg (i.v.) | | 2.7 (1.9–4.0)* |
| | 3 | 0.8 μmol/kg (i.v.) | | 2.3 (1.7–3.1)* |
| | 1 | 0.4 nmol/kg (i.c.v.) | | 2.6 (1.9–3.9)* |
| | 1 | 12.5 μmol/kg (i.v.) | | 6.7 (4.6–10.0)* |

[a]Peak antinociceptive activity times of agonists were: morphine (30 min), U50,488H (20 min), DSLET (10 min) and DPDPE (20 min).
[b]Antagonists were administered so that their peak activities coincided with the peak agonist activities. Pretreatment times were: 2 (30 min i.c.v., 90 min i.v.), 3 (20 min i.c.v., 30 min i.v.) and 1 (30 min i.c.v., 40 min i.v.).
[c]Antinociceptive activities were determined by tail flick assay in mice.
[d]$ED_{50}$ with antagonist/control $ED_{50}$.

The doses required to produce equivalent antagonism i.c.v. and i.v. are listed in Table 5. These doses were determined by calculating the dose of antagonist required to double the $ED_{50}$ dose of DPDPE. The i.v./i.c.v. dose ratios of 2 and 3 were 15- and 7-times greater than that of NTI.

Both 2 and 3 were $\delta_1$ selective in that they antagonized the $\delta_1$ agonist, DPDPE, but not the $\delta_2$ agonist, DSLET. It is not entirely clear why the binding selectivity of 2 and 3 differ from their pharmacologic selectivity, but one possibility is that accessibility to the $\delta_1$ subtype in vivo might be favored by the presence of hydrophilic groups in these compounds. Thus, it is conceivable that the greater water solubility of the conjugates might facilitate access to tissue compartments in the CNS that contain $\delta_1$ sites or prevent access to compartments that contain $\delta_2$ sites. An alternate possibility is that identical $\delta$ receptors are located in different tissue compartments whose accessibility is governed by the polarity of the antagonist. Significantly, the in vivo $\delta_2$-selective antagonists, naltriben (NTB) and benzylnaltrindole, are considerably more lipophilic than 2 or 3. See Q. Jiang et al., *J. Pharmacol. Exp.*, 257, 1069 (1991) and V. L. Korlipara et al., *J. Med. Chem.*, 37, 1882 (1994).

As shown on Table 4, the i.v./i.c.v. dose ratios of 2 and 3 to produce equivalent antagonism of DPDPE-induced antinociception were very high (>49,000) and, as expected, greater than that determined for NTI. This ratio was 15- and 7-fold greater than that of NTI for 2 and 3, respectively, which indicates that NTI penetrates the CNS more readily than the conjugates. It was surprising that the aspartate 3 has a lower i.v./i.c.v. dose ratio than the glycinate 2 in view of the greater polarity of the aspartate relative to the glycinate residue.

In summary, amino acid conjugates 2 and 3 are highly potent $\delta$ opioid antagonists when administered centrally, and many orders of magnitude less potent when delivered by the peripheral route. The in vivo $\delta_1$ selectivity of 2 and 3 may be a function of the greater hydrophilic character imparted to the ligands by the amino acid residue. If, for example, this promotes greater accessibility of the ligand to the $\delta_1$ receptor subtype in neural tissues, it may suggest a new approach to the design of in vivo pharmacologically selective antagonist ligands for $\delta$ opioid receptor subtypes localized in the CNS. If the origin of the pharmacologic selectivity of NTI analogs for central $\delta$ opioid receptor subtypes is in part related to selective access to tissue compartments rather than to binding selectivity, this would explain the lack of correlation between in vivo pharmacologic selectivity and binding selectivity. For this reason, the subtype selectivity of compounds such as 2 and 3 for antagonism of antinociception may not be the same for $\delta$ receptors at peripheral sites.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula:

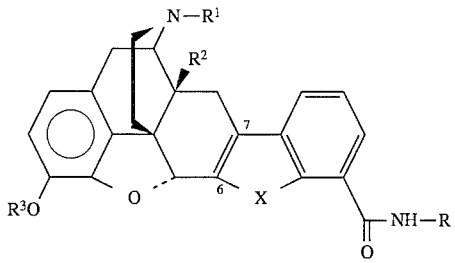

wherein $R^1$ is $(C_1-C_5)$alkyl, $(C_6-C_{12})$aryl, trans$(C_4-C_5)$alkenyl, allyl; $C_3-C_6$(cycloalkyl)alkyl, $C_5-C_7$(cycloalkenyl)alkyl, $(C_6-C_{12})$aralkyl or furan-2-ylalkyl, wherein alkyl is $(C_1-C_5)$alkyl; $R^2$ is H, OH or $O_2C(C_1-C_5)$alkyl; $R^3$ is H, $(C_6-C_{10})$aralkyl, wherein alkyl is $(C_1-C_5)$alkyl, $(C_1-C_5)$alkyl or $(C_1-C_5)$alkylCO; X is O, S or NY, wherein Y is H, benzyl or $(C_1-C_5)$alkyl; R is CH(Z)CO$_2$Y, wherein Z is H, CH$_2$CO$_2$Y or $(CH_2)_nN(R^4)(R^5)$, wherein n is an integer of 1 to 5 and $R^4$ and $R^5$ are individually H, $(C_1-C_4)$alkyl, phenyl, (C=NH)NH$_2$, benzyloxycarbonyl or (C=NHNO$_2$); or a pharmaceutically acceptable salt thereof.

2. The compound of claim 1 wherein $R^1$ is $C_3-C_6$(cycloalkyl)-$C_1-C_5$ (alkyl).

3. The compound of claim 2 wherein $R^1$ is $C_3-C_6$(cycloalkyl)-methyl.

4. The compound of claim 3 wherein $R^1$ is cyclopropylmethyl.

5. The compound of claim 1 wherein $R^2$ is OH or OAc.

6. The compound of claim 5 wherein $R^3$ is H.

7. The compound of claim 1 wherein X is NH, N(benzyl) or NCH$_3$.

8. The compound of claim 1 wherein Y is H.

9. The compound of claim 8 wherein $R^4$ and $R^5$ are H.

10. The compound of claim 9 wherein $R^4$ is H and $R^5$ is (C=NH)NH$_2$.

11. The compound of claim 9 wherein n is 3 or 4.

12. A compound of the formula:

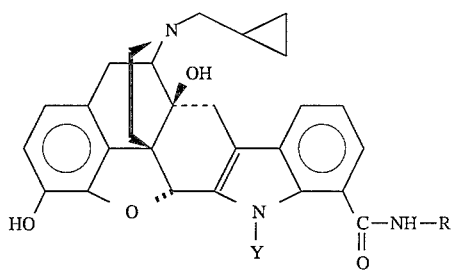

wherein

Y is H, CH$_3$ or benzyl; R is CH(Z)CO$_2$Y, wherein Z is H, CH$_2$CO$_2$Y or $(CH_2)_{3-4}$NHR$^4$, wherein $R^4$ is H or (C=NH)NH$_2$; and the pharmaceutically acceptable salts thereof.

13. The compound of claim 12 wherein Y is H.

14. The compound of claim 12 wherein $R^4$ is H.

15. The compound of claim 14 wherein $R^4$ is (C=NH)NH$_2$.

16. The compound of claim 12 wherein Z is CH$_2$CO$_2$H.

17. 7'-(Carboxamidoglycine)-17-(cyclopropyhnethyl)-6,7-dehydro-3,14-dihydroxy-4,5α-epoxy-6,7,2',3'-indolomorphinan.

18. 7'-(Carboxamido-L-aspartate)-17-(cyclopropylmethyl)-6,7-dehydro-3,14-dihydroxy-4,5α-epoxy-6,7,2',3'-indolomorphinan.

19. 7'-(Carboxamido L-ornithine)-17-(cyclopropylmethyl)-6,7-dehydro-3,14-dihydroxy-4,5α-epoxy-6,7,2',3'-indolomorphinan hydrochloride.

20. 7'-(Carboxamido-L-arginine)-17-(cyclopropylmethyl)-6,7-dehydro-3,14-dihydroxy-4,5α-epoxy-6,7,2',3'-indolomorphinan hydrochloride.

21. 7'-(N(α)-Carboxamido-L-lysine)-17-(cyclopropylmethyl)-6,7-dehydro-3,14-dihydroxy-4,5α-epoxy-6,7,2',3'-indolomorphinan hydrochloride.

* * * * *

UNITED STATES PATENT AND TRADEMARK OFFICE
CERTIFICATE OF CORRECTION

Page 1 of 2

PATENT NO. : 5,578,725
DATED : November 26, 1996
INVENTOR(S) : Philip S. Portoghese et al.

It is certified that error appears in the above-indentified patent and that said Letters Patent is hereby corrected as shown below:

In the ABSTRACT, line 7, please delete "alky" and insert --alkyl--.

In Column 6, line 41, Example 1, please delete "$^{13}$NMR" and insert --$^{13}$CNMR--.

In Column 6, line 51, Example 2, please delete "cycloptopylmethyl" and insert --cyclopropylmethyl--.

In Column 7, line 41, Example 3, please delete "$H_2O$" and insert --$H_{20}$--.

In Column 8, line 6, Example 4, please delete "156,87" and insert --156.87--.

In Column 10, line 29, please delete "H21" and insert --$H_{21}$--.

UNITED STATES PATENT AND TRADEMARK OFFICE
CERTIFICATE OF CORRECTION

PATENT NO. : 5,578,725
DATED : November 26, 1996
INVENTOR(S) : Philip S. Portoghese et al.

It is certified that error appears in the above-indentified patent and that said Letters Patent is hereby corrected as shown below:

At Column 12, line 48, please delete "nad" and insert --and--.

At Column 12, line 67, please delete "in vitro or in vivo" and insert --*in vitro* or *in vivo*--.

At Column 13, line 27, please delete "trans" and insert --*trans*--.

At Column 14, line 31, please delete "in vivo" and insert --*in vivo*--.

At Column 15, line 26, please delete "in vivo" and insert --*in vivo*--.

At Column 15, line 37, please delete "in vivo" and insert --*in vivo*--.

Signed and Sealed this

Eighteenth Day of November 1997

Attest:

BRUCE LEHMAN

*Attesting Officer*         *Commissioner of Patents and Trademarks*